United States Patent [19]

Helsley

[11] 3,968,217

[45] July 6, 1976

[54] 5-(3-)SUBSTITUTED-10,11-DIHYDRO-5H-DIBENZ[b,f]AZEPINES

[75] Inventor: Grover C. Helsley, Pottersville, N.J.

[73] Assignee: A. H. Robins Company, Incorporated, Richmond, Va.

[22] Filed: Jan. 16, 1975

[21] Appl. No.: 541,683

Related U.S. Application Data

[62] Division of Ser. No. 462,944, April 22, 1974, Pat. No. 3,886,170.

[52] U.S. Cl. .............................................. 424/267
[51] Int. Cl.² ..................................... A61K 31/445
[58] Field of Search ................................... 424/267

Primary Examiner—Stanley J. Friedman

[57] ABSTRACT

5-(3-)Substituted-10,11-dihydro-5H-dibenz[b,f]azepines useful as antidepressants and methods of preparation are disclosed.

8 Claims, No Drawings

5-(3-)SUBSTITUTED-10,11-DIHYDRO-5H-DIBENZ[B,F]AZEPINES

This is a division of application Ser. No. 462,944, filed Apr. 22, 1974, now U.S. Pat. No. 3,886,170.

The present invention concerns 10,11-dihydro-5H-dibenz [b,f]azepines and is more particularly concerned with 5-(3-) substituted-10,11-dihydro-5H-dibenz[b,f]azepines, compositions containing the same as active ingredients and methods of making and using the same.

The novel compounds of the present invention correspond to the general Formula I:

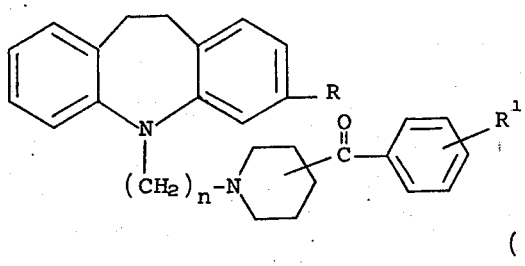

wherein;
R represents hydrogen, bromine, chlorine, methoxy, trifluoromethyl, sulfamoyl, or N,N-dimethylsulfamoyl,
$R^1$ represents hydrogen, lower alkoxy, lower alkyl, trifluoromethyl, or halogen having an atomic weight less than 80,
n is a positive integer from 2-4 inclusive, and
non-toxic pharmaceutically acceptable acid addition salts thereof.

The present invention contemplates various embodiments as can be seen from Formula I and the respective values assigned to the symbols R, $R^1$ and n.

In one embodiment of the present invention the value of n can be 2 through 4 inclusive and R is hydrogen, while in another embodiment n can have the value of 3 or 4 and R is chlorine, bromine or fluorine.

Another embodiment of the invention contemplates compounds wherein n is 3, R is chlorine, bromine, or fluorine, and the benzoyl moiety is attached to the 3 to 4 position of the piperidine nucleus.

A preferred embodiment of the present invention is the compound wherein n is 3, R is fluorine and the benzoyl moiety is attached to the 4 position of the piperidine ring.

The antidepressant profile is established by:
a. administration of the compounds intraperitoneally to mice at dose levels of 10, 20 and 40 mg/kg followed by the administration (i.p.) of 300 mg/kg of l-Dopa [3-(3,4-dihydroxyphenyl)-6-alanine] 60 min. after the test compound. The ratio of the number of dead mice to the number of mice used (24 hrs.) is indicative of the potency of the test drug as an anti-depressant. The test is controlled by the use of the known antidepressant amitriptyline.

b. administration of the compounds intraperitoneally (mg/kg) to muricidal rats. Mice are put into the rat's cage and the ratio of the number muricidal to the number used measures the effectiveness of the test compound as an antidepressant. Major tranquilizers are ineffective in suppressing muricidal rats.

The compound 5-{3-[4-(4-fluorobenzoyl)-piperidinyl]propyl}-10,11-dihydro-5H-dibenz[b,f]azepine was shown to have antidepressant properties when used in the hereinabove described procedures.

It is, therefore, an object of the present invention to provide novel 5-(3-)substituted-10,11-dihydro-5H-dibenz[b,f]azepines. A further object is to provide novel 5-(3-)substituted-10,11-dihydro-5H-dibenz[b,f]azepines having antidepressant activity. A still further object is to provide methods for producing the novel compounds, pharmaceutical compositions containing said compounds as active ingredients and methods for the utilization thereof. Additional objects will be apparent to one skilled in the art and still other objects will be apparent hereinafter.

The term "lower-alkyl" as used in the specification and claims includes straight and branched chain radicals of up to eight carbon atoms inclusive and is exemplified by such groups as methyl, ethyl, propyl, isopropyl, butyl, isobutyl, tertiary butyl, amyl, isoamyl, hexyl, heptyl and octyl.

The term "lower-alkoxy" has the formula -O-lower-alkyl.

The compounds of the invention are preferably employed in the form of non-toxic pharmaceutically acceptable acid addition salts. Such salts have improved water solubility over the free base. Although the non-toxic salts are preferred, any salt may be prepared for use as a chemical intermediate, as in the preparation of another acid addition salt suitable for administration to an animal body for the desired physiological effect thereof. Appropriate pharmaceutically acceptable acid addition salts are those derived from inorganic acids such as hydrochloric, hydrobromic, sulfuric and phosphoric, and organic acids such as acetic, citric, lactic, maleic, oxalic, fumaric and tartaric. The preferred addition salts are the hydrochloride, maleate, fumarate and oxalate. The acid addition salts of the product compounds are conventionally prepared by reaction of the basic compounds with the acid, either or both of which may be in the form of ether, alcohol or acetone solutions.

The starting materials used in preparing the novel compounds of Formula I are the compounds of Formula II, namely, 10,11-dihydro-5H-dibenz[b,f]azepines and the 3-substituted derivatives thereof which are commercially available or which can be prepared by known procedures described in the chemical literature.

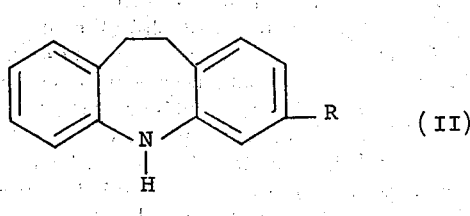

The benzoylpiperidines used in preparing the novel compounds of the present invention are also known compounds or can readily be prepared according to the procedures described in U.S. Pat. No. 3,576,810.

The preparation of the novel 5-(3-)substituted-10,11-dihydro-5H-dibenz[b,f]azepines may be accomplished by mixing and reacting a selected 10,11-dihydro-5H-dibenz[b,f]azepine (II) with an α,ω-dihalo alkane (III), preferably an α-chloro-ω-bromoalkane, to give a 5-(3-)(ω-haloalkanyl)-10,11-dihydro-5H- dibenz[b,f]azepine (IV) which is reacted with a selected benzoylpiperidine (V). The reaction sequence is as follows:

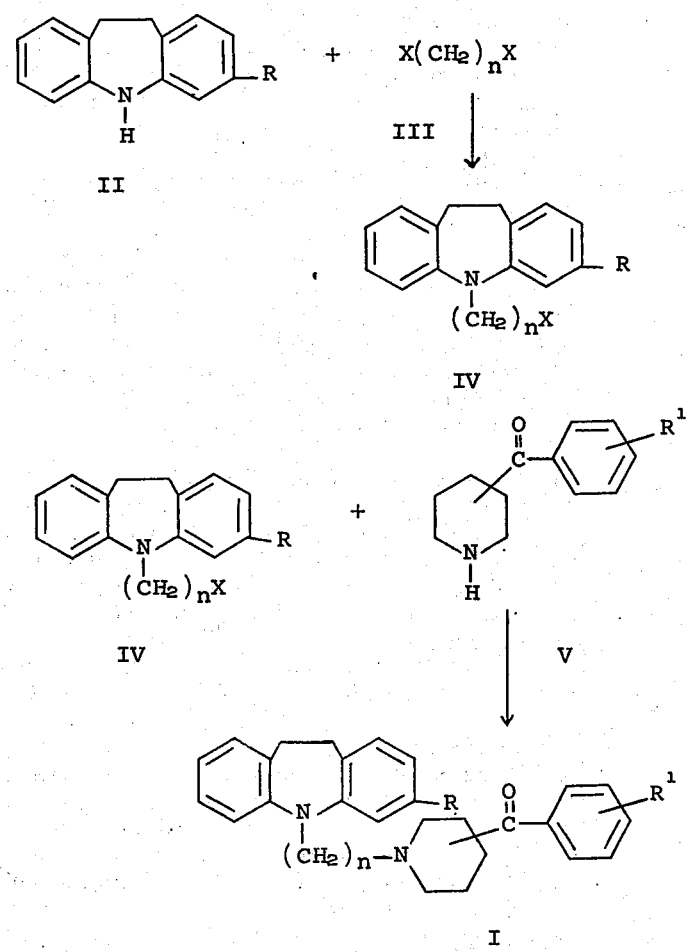

wherein R, R¹ and n have the values previously assigned, and X is halogen, preferably bromine or chlorine.

A general method for the preparation of the novel compounds of Formula I is as follows.

A stirred suspension of alkyl lithide, or an alkali metal amide as, for example, butyl lithium or sodium amide in a suitable organic solvent such as toluene, and a selected 10,11-dihydro-5H-dibenz[b,f]azepine (II) is refluxed for a period of from about four to about six hours and then an α,ω-dihaloalkane (III) is added and refluxing is continued for a period of from about eight hours to about 16 hours. The reaction mixture is worked up by acid-base extraction and the 5-(ω-haloalkyl)-10,11-dihydro-5H-dibenz[b,f]azepine (IV) is isolated by conventional procedures such as crystallization or chromatography, preferably by distillation under reduced pressure. A stirred mixture of the 5-(ω-haloalkyl)-10,11-dihydro-5H-dibenz[b,f]azepine (IV), a selected benzoylpiperidine (V) and potassium carbonate in suitable solvent as, for example, n-butanol or dimethylformamide is heated at a temperature of from about 80°C. to about 110°C., preferably at about 90°C. to about 100°C. for a period of from about 14 hours to about 20 hours. The cooled reaction mixture is filtered free of solids, the solvent is removed at reduced pressure, the residual material dissolved in a suitable organic solvent, illustratively ether, the solution filtered and the 5-[ω-(benzoylpiperidinyl)alkyl]-10,11-dihydro-5H-dibenz[b,f]azepine (I) is isolated by a suitable procedure as, for example, distillation, chromotography, crystallization or by conversion to a suitable acid addition salt.

3-Substituted-10,11-dihydro-5H-dibenz[b,f]azepines which can be used in the present invention include:

3-bromo-10,11-dihydro-5H-dibenz[b,f]azepine,
3-chloro-10,11-dihydro-5H-dibenz[b,f]azepine,
3-methoxy-10,11-dihydro-5H-dibenz[b,f]azepine,
3-trifluoromethyl-10,11-dihydro-5H-dibenz[b,f]azepine,
3-sulfamoyl-10,11-dihydro-5H-dibenz[b,f]azepine, and
3-(N,N-dimethylsulfamoyl)-10,11-dihydro-5H-dibenz[b,f]azepine.

Benzoylpiperidines which can be used in the present invention include:

3-benzoylpiperidine,
4-benzoylpiperidine,
4-(4-fluorobenzoyl)piperidine,
4-(4-chlorobenzoyl)piperidine, 4-(4-bromobenzoyl)piperidine,
4-(3-trifluoromethylbenzoyl)piperidine,
3-(4-fluorobenzoyl)piperidine,
3-(4-chlorobenzoyl)piperidine,
3-(3-trifluoromethylbenzoyl)piperidine,
4-(4-methylbenzoyl)piperidine,
4-(4-methoxybenzoyl)piperidine,
3-(4-ethylbenzoyl)piperidine,
3-(4-methoxybenzoyl)piperidine, and
4-(4-bromobenzoyl)piperidine.

PREPARATION 1

5-(3-Chloropropyl)-10,11-dihydro-5H-dibenz[b,f]azepine.

A solution of 10,11-dihydro-5H-dibenz[b,f]azepine (19.5 gms.; 0.10 moles) in dry ether was added to a solution of 7.7 gms. (0.12 mole) of butyl lithium in hexane. The stirred solution was warmed for approximately one hour and then 31.0 gms. (0.20 mole) of bromopropylchloride in ether was added and the resulting mixture heated at reflux for 16 hours. Aliquot analysis showed no reaction had taken place. Approximately one liter of toluene was added to the reaction mixture, lower boiling solvents were removed by distillation and the reaction mixture heated at reflux with stirring for 12 hours. On working up the reaction mixture, there was obtained 7.0 gms. of 5-(3-chloropropyl)-10,11-dihydro-5H-dibenz[b,f]azepine which distilled at 150°–153°C. (0.03 mm.). An additional 6.0 gms. of impure material which contained approximately 15% of unreacted 10,11-dihydro-5H-dibenz[b,f]azepine was obtained which distilled at 140°–150°C. (0.03 mm.).

EXAMPLE 1

5-{3-[4-(4-Fluorobenzoyl)piperidinyl]propyl}-10,11-dihydro5H-dibenz[b,f]azepine.

A stirred mixture containing 4.5 gms. (0.017 mole) of 5-(3-chloropropyl)-10,11-dihydro-5H-dibenz[b,f]azepine, 3.4 gms (0.017 mole) of 4-(4-fluorobenzoyl)piperidine, 10.0 gms. of potassium carbonate and 75 ml. of dimethylformamide was heated at 90°–100°C. for 16 hours. The cooled suspension was filtered, the solvent removed at reduced pressure and the residual oil was taken up in ether and filtered to remove insoluble materials. The clear filtrate was treated with a solution of 2.1 gms. (0.017 mole) of oxalic acid dihydrate in isopropanol. The oxalate which separated on cooling was collected by filtration. The salt melted at 150°–155°C. and weighed 2.9 gms. (32% yield). After recrystallization from isopropanol the salt melted at 156°–159°C.

Analysis: Calculated for $C_{31}H_{33}N_2O_5F$: C,69.91; H,6.24; N,5.26. Found: C,70.03; H,6.30; N,5.31.

Effective quantities of any of the foregoing pharmacologically active compounds of Formula I may be administered to a living animal body for therapeutic purposes according to usual modes of administration and in usual forms, such as orally in solutions, emulsions, suspensions, pills, tablets and capsules in pharmaceutically acceptable carriers and parenterally in the form of sterile solutions.

For the parenteral administration the carrier or excipient may be a sterile, parenterally acceptable liquid; e.g., water or a parenterally acceptable oil; e.g., arachis oil contained in ampules.

Although very small quantities of the active materials of the present invention are effective when minor therapy is involved or in cases of administration to subjects having a relatively low body weight, unit dosages are usually from five milligrams or above and preferably 25, 50, or 100 milligrams or even higher, depending, of course, upon the emergency of the situation and the particular result desired. Five to 50 milligrams appears optimum per unit dose or usual broader ranges appear to be one to 500 milligrams per unit dose. Daily dosages should preferably range from 10 mg. to 100 mg. The active ingredients of the invention may be combined with other pharmacologically active agents as stated above. It is only necessary that the active ingredient constitute an effective amount, i.e., such that a suitable effective dosage will be obtained consistent with the dosage form employed. Obviously, several unit dosage forms may be administered at about the same time. The exact individual dosages as well as daily dosages will, of course, be determined according to standard medical principles under the direction of a physician or veterinarian.

The following formulations are representative for all of the pharmacologically active compounds of this invention.

FORMULATIONS

1. Capsules

Capsules of 5 mg., 10 mg., 25 mg., and 50 mg. of active ingredient per capsule are prepared. With the higher amounts of active ingredient, reduction may be made in the amount of lactose.

| Typical blend for encapsulation | Per Capsule, mg. |
| --- | --- |
| Active ingredient, as salt | 5 |
| Lactose | 259 |
| Starch | 126 |
| Magnesium stearate | 4 |
| Total | 394 |

Additional capsule formulations preferably contain a higher dosage of active ingredient and are as follows:

| Ingredients | 100 mg. per Capsule | 250 mg. per Capsule | 500 mg. per Capsule |
| --- | --- | --- | --- |
| Active ingredient, as salt | 100 | 250 | 500 |
| Lactose | 214 | 163 | 95 |
| Starch | 87 | 81 | 47 |
| Magnesium stearate | 4 | 6 | 8 |
| Total | 399 | 500 | 650 |

In each case, uniformly blend the selected active ingredient with lactose, starch, and magnesium stearate and encapsulate the blend.

2. Tablets

A typical formulation for a tablet containing 5.0 mg. of active ingredient per tablet follows. The formulation may be used for other strengths of active ingredient by adjustment of weight of dicalcium phosphate.

| | Per Tablet, mg. |
| --- | --- |
| 1. Active ingredient | 5.0 |
| 2. Corn starch | 15.0 |
| 3. Corn starch (paste) | 12.0 |
| 4. Lactose | 35.0 |
| 5. Dicalcium phosphate | 132.0 |

| (continued) | Per Tablet, mg. |
|---|---|
| 6. Calcium stearate | 2.0 |
| Total | 202.0 |

Uniformly blend 1, 2, 4, and 5. Prepare 3 as a 10 percent paste in water. Granulate the blend with starch paste and pass the wet mass through an eight mesh screen. The wet granulation is dried and sized through a twelve mesh screen. The dried granules are blended with the calcium stearate and compressed.

| (3) Injectable - 2% sterile solution | Per cc |
|---|---|
| Active ingredient mg. | 20 |
| Preservative, e.g. chlorobutanol, wt./vol . . . percent | 0.5 |
| Water for injection q.s. | |

Prepare solution, clarify by filtration, fill into vials, seal and autoclave.

What is claimed is:

1. A pharmaceutical composition having antidepressant activity, in dosage unit form, comprising a pharmaceutical carrier and an antidepressant amount of a 5-(3-)substituted-10,11-dihydro-5H-dibenz [b,f] azepine having the formula:

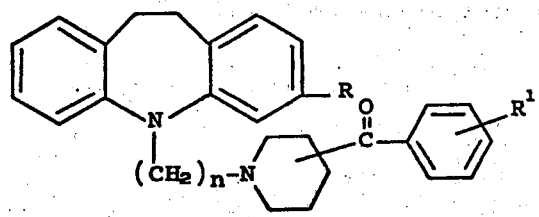

wherein;
R is selected from the group consisting of hydrogen, bromine, chlorine, methoxy, trifluoromethyl, sulfamoyl and N,N-dimethylsulfamoyl,
$R^1$ is selected from the group consisting of hydrogen, lower alkoxy, lower alkyl, trifluoromethyl and halogen having an atomic weight less than 80,
$n$ is a positive integer from 2–4 inclusive, or a pharmaceutically acceptable acid addition salt thereof.

2. The antidepressant composition as defined in claim 1, wherein the active ingredient is in the form of a pharmaceutically acceptable acid addition salt.

3. The antidepressant composition as defined in claim 2, wherein the active ingredient is present in the amount of from 5 to 500 milligrams.

4. The antidepressant composition as defined in claim 3, wherein the active ingredient is 5-{3-[4-(4fluorobenzoyl) piperidinyl]propyl}-10,11-dihydro-5H-dibenz azepine oxalate.

5. A method for treating depression in a host comprising administering to a host suffering from depression an effective amount of a compound having the formula:

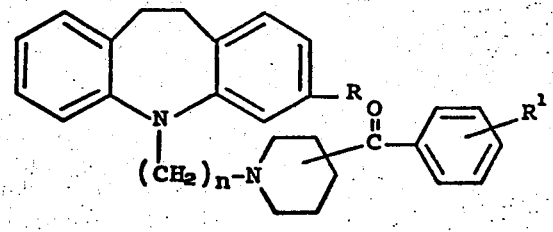

wherein;
R is selected from the group consisting of hydrogen, bromine, chlorine, methoxy, trifluoromethyl, sulfamoyl and N,N-dimethylsulfamoyl,
$R^1$ is selected from the group consisting of hydrogen, lower alkoxy, lower alkyl, trifluoromethyl and halogen having an atomic weight less than 80,
$n$ is a positive integer from 2–4 inclusive, or a pharmaceutically acceptable acid addition salt thereof.

6. The method according to claim 5 wherein the active ingredient is in the form of a pharmaceutically acceptable acid addition salt.

7. The method according to claim 6 wherein the active ingredient is administered together with a pharmaceutically acceptable carrier therefor and in an amount of about one to 500 milligrams.

8. The method according to claim 7 wherein the active ingredient is 5-{3-[4-(4-fluorobenzoyl)-piperidinyl]propyl}10,11-dihydro-5H-dibenz[b,f]azepine oxalate.

* * * * *